United States Patent
Su

(10) Patent No.: US 9,381,012 B2
(45) Date of Patent: Jul. 5, 2016

(54) ILLUMINATED SURGICAL RETRACTOR SYSTEM AND MAGNETICALLY-CONTROLLED ILLUMINATION DEVICE

(71) Applicant: Chi Mei Medical Center, Tainan (TW)

(72) Inventor: Ying-Chieh Su, Tainan (TW)

(73) Assignee: Chi Mei Medical Center, Tainan (TW)

( * ) Notice: Subject to any disclaimer, the term of this patent is extended or adjusted under 35 U.S.C. 154(b) by 0 days.

(21) Appl. No.: 14/562,369

(22) Filed: Dec. 5, 2014

(65) Prior Publication Data
US 2015/0157307 A1  Jun. 11, 2015

(30) Foreign Application Priority Data
Dec. 10, 2013 (TW) .................................. 102145416

(51) Int. Cl.
*A61B 1/32* (2006.01)
*A61B 17/02* (2006.01)
*A61B 1/045* (2006.01)
*A61B 1/06* (2006.01)

(52) U.S. Cl.
CPC ............. *A61B 17/0293* (2013.01); *A61B 1/045* (2013.01); *A61B 1/0615* (2013.01)

(58) Field of Classification Search
CPC ................ A61F 2/3423; A61F 2/3431; A61F 2017/3419; A61F 17/0293; A61F 1/06; A61F 1/0607; A61F 1/0615; A61F 1/00096; A61F 1/042; A61F 1/043; A61F 1/045; A61F 19/5202
USPC .................................................. 600/301–346
See application file for complete search history.

(56) References Cited

U.S. PATENT DOCUMENTS

| 3,302,014 | A | 1/1967 | Moore et al. | |
|---|---|---|---|---|
| 5,321,501 | A * | 6/1994 | Swanson | A61B 1/00096 250/227.27 |
| 2002/0096956 | A1 | 7/2002 | Erten | |
| 2002/0122246 | A1* | 9/2002 | Tearney | A61B 1/00096 359/368 |
| 2002/0165444 | A1* | 11/2002 | Whitman | A61B 1/00027 600/407 |
| 2003/0073998 | A1* | 4/2003 | Pagliuca | A61B 17/0218 606/86 A |
| 2004/0215059 | A1* | 10/2004 | Homan | A61B 1/041 600/160 |
| 2005/0154294 | A1* | 7/2005 | Uchiyama | A61B 1/00029 600/420 |
| 2006/0247500 | A1 | 11/2006 | Voegele et al. | |
| 2007/0238955 | A1* | 10/2007 | Tearney | A61B 1/00096 600/407 |
| 2008/0097163 | A1* | 4/2008 | Butler | A61B 1/32 600/208 |
| 2008/0103366 | A1* | 5/2008 | Banchieri | A61B 1/32 600/208 |

(Continued)

Primary Examiner — Ellen C Hammond
Assistant Examiner — Stuart S Bray
(74) Attorney, Agent, or Firm — Cesari and McKenna LLP

(57) ABSTRACT

An illuminated surgical retractor system includes a surgical retractor and at least one illumination device. The surgical retractor includes an outer ring, a light-transmissive hollow inner ring, and a tubular retraction membrane which extends between the output ring and the inner ring and which has a first open end connected to and spread open by the outer ring and a second open end connected to and spread open by the inner ring. The illumination device is disposed in the inner ring and is operable to emit a light beam. The illumination device includes a magnetic component which is responsive to an applied magnetic field to cause the illumination device to change a direction in which the light beam is emitted.

20 Claims, 12 Drawing Sheets

(56) References Cited

U.S. PATENT DOCUMENTS

| | | | | |
|---|---|---|---|---|
| 2009/0248041 A1* | 10/2009 | Williams | A61B 8/12 | 606/130 |
| 2010/0085466 A1* | 4/2010 | Fujimori | A61B 1/00096 | 348/340 |
| 2010/0286487 A1* | 11/2010 | Van Lue | A61B 17/3462 | 600/249 |
| 2011/0028790 A1* | 2/2011 | Farr | A61B 1/00052 | 600/187 |
| 2011/0098530 A1* | 4/2011 | Yamane | A61B 1/00172 | 600/109 |
| 2012/0238830 A1* | 9/2012 | Vukeljic | G02B 6/3817 | 600/249 |
| 2012/0259204 A1* | 10/2012 | Carrat | A61B 5/061 | 600/414 |
| 2013/0018230 A1* | 1/2013 | Su | A61B 1/0607 | 600/208 |
| 2013/0079645 A1* | 3/2013 | Amirana | A61B 5/0084 | 600/479 |
| 2013/0102862 A1* | 4/2013 | Mercader | A61B 5/1459 | 600/317 |
| 2013/0204095 A1* | 8/2013 | Mark | A61B 17/320016 | 600/249 |
| 2014/0028924 A1* | 1/2014 | Yamaguchi | G02F 1/29 | 349/1 |
| 2014/0081083 A1* | 3/2014 | Morita | A61B 1/0646 | 600/109 |
| 2014/0114140 A1* | 4/2014 | Ellman | A61B 17/0206 | 600/249 |
| 2014/0275768 A1* | 9/2014 | Luttati | A61B 1/00096 | 600/104 |
| 2014/0288427 A1* | 9/2014 | Wall | A61B 1/3135 | 600/439 |
| 2014/0357956 A1* | 12/2014 | Salahieh | A61B 1/05 | 600/160 |
| 2015/0037201 A1* | 2/2015 | Armour | A61B 19/38 | 422/3 |
| 2015/0073227 A1* | 3/2015 | Teder | A61B 1/06 | 600/249 |
| 2015/0141755 A1* | 5/2015 | Tesar | A61B 19/26 | 600/111 |
| 2015/0148602 A1* | 5/2015 | Hill | A61B 1/00147 | 600/109 |
| 2015/0223674 A1* | 8/2015 | Wieters | A61B 1/00096 | 74/89 |
| 2015/0250555 A1* | 9/2015 | Haverich | A61B 19/5202 | 600/245 |
| 2015/0272693 A1* | 10/2015 | Emodi | A61B 19/5202 | 600/249 |
| 2015/0282692 A1* | 10/2015 | Wieters | A61B 1/00068 | 604/95.05 |
| 2015/0289947 A1* | 10/2015 | Crawford | A61B 19/5202 | 600/249 |
| 2015/0305938 A1* | 10/2015 | Vold | A61K 35/74 | 606/6 |
| 2016/0000307 A1* | 1/2016 | Akimoto | A61B 1/04 | 600/109 |
| 2016/0000500 A1* | 1/2016 | Salahieh | A61B 18/1492 | 600/104 |
| 2016/0008088 A1* | 1/2016 | Vayser | A61B 19/08 | 600/178 |
| 2016/0015253 A1* | 1/2016 | Roop | A61B 17/1285 | 600/106 |

* cited by examiner

ILLUMINATED SURGICAL RETRACTOR SYSTEM AND MAGNETICALLY-CONTROLLED ILLUMINATION DEVICE

CROSS-REFERENCE TO RELATED APPLICATIONS

This application claims priority of Taiwanese Patent Application No. 102145416, filed on Dec. 10, 2013, the entire disclosure of which is incorporated herein by reference.

BACKGROUND OF THE INVENTION

1. Field of the Invention

The invention relates to a surgical retractor system and an illumination device, more particularly to an illuminated surgical retractor system and a magnetically-controlled illumination device.

2. Background Information

During a surgical operation, such as a laparotomy operation, a surgical retractor is commonly used for retracting an incision through an abdominal wall such that a surgical instrument or an operator's hand may gain access into the abdominal cavity to perform the surgical operation. However, since light beams provided by a conventional surgical light system that is disposed above a patient are usually blocked by the surgical instrument or the operator's hand accessing into the abdominal cavity via the surgical retractor during the laparotomy operation, the abdominal cavity may not be sufficiently illuminated and performance of the surgical operation is thus adversely influenced. Even though a light delivery component of an endoscope may be used for illumination, a range and an intensity of illumination provided by the endoscope are still limited, and may be insufficient for the surgical operations.

In view of this, a conventional surgical retractor is provided with an illumination device which is disposed in a portion of the conventional surgical retractor which is arranged inside a body cavity so as to promote brightness in the body cavity. However, the illumination device of the conventional retractor emits light beams only at a fixed direction, and an illumination direction of the illumination device is not adjustable according to different needs. For example, the direction of the light beams cannot be adjusted to focus on a target to be subjected to the surgical operation.

SUMMARY OF THE INVENTION

Therefore, an object of the present invention is to provide an illuminated surgical retractor system and a magnetically-controlled illumination device each of which emits a light beam in a direction that is adjustable by an applied magnetic field.

According to a first aspect of the present invention, the illuminated surgical retractor system comprises a surgical retractor, and at least one illumination device. The surgical retractor includes an outer ring, a light-transmissive hollow inner ring, and a tubular retraction membrane which extends between the output ring and the inner ring and which has a first open end connected to and spread open by the outer ring and a second open end connected to and spread open by the inner ring. The illumination device is disposed in the inner ring and is operable to emit a light beam. The illumination device includes a magnetic component which is responsive to an applied magnetic field to cause the illumination device to change a direction in which the light beam is emitted.

According to a second aspect of the present invention, the magnetically-controlled illumination device comprises a light-transmissive inner casing, a light-emitting unit, a lens element, and a magnetic component. The light-transmissive inner casing defines a receiving space. The light-emitting unit is mounted to the inner casing and is configured to emit a light beam toward the receiving space. The lens element is movably disposed in the receiving space and is rotatable with respect to the inner casing. The lens element is configured to guide the light beam emitted by the light-emitting unit outwardly of the inner casing. The magnetic component is mounted to the lens element, and is driven by an applied magnetic field to rotate the lens element with respect to the light-emitting unit such that a direction in which the light beam propagates outwardly of the inner casing is changed by the lens element.

According to a third aspect of the present invention, the magnetically-controlled illumination device comprises an outer casing unit, a light-transmissive inner casing, a light-emitting unit, a lens element, and a magnetic component. The outer casing unit includes a light-transmissive outer casing which defines a spherical space. The light-transmissive inner casing is movably disposed in the spherical space and is rotatable with respect to the outer casing unit. The inner casing defines a receiving space. The light-emitting unit is mounted to the inner casing, and is configured to emit the light beam toward the receiving space. The lens element is mounted to the inner casing at a position corresponding to the light-emitting unit. The lens element is configured to guide the light beam emitted by the light-emitting unit outwardly of the inner casing and the outer casing. The magnetic component is mounted to the inner casing, and is driven by an applied magnetic field to rotate the inner casing with respect to the outer casing unit and thereby move the light-emitting unit together with the lens element such that the direction in which the light beam is emitted outwardly of the outer casing is changed.

An effect of the present invention resides in that, by virtue of the magnetic component provided in the illumination device which is disposed in the surgical retractor, the direction in which the light beam is emitted may be adjusted according to the applied magnetic field, so as to satisfy different needs for illumination. In this way, the light beam emitted by the illumination device may be directed to the desired direction, and thereby provide sufficient illumination on a specific portion in the body cavity.

BRIEF DESCRIPTION OF THE DRAWINGS

Other features and advantages of the present invention will become apparent in the following detailed description of embodiments with reference to the accompanying drawings, of which.

DETAILED DESCRIPTION OF AN ILLUSTRATIVE EMBODIMENT

Figure 1:
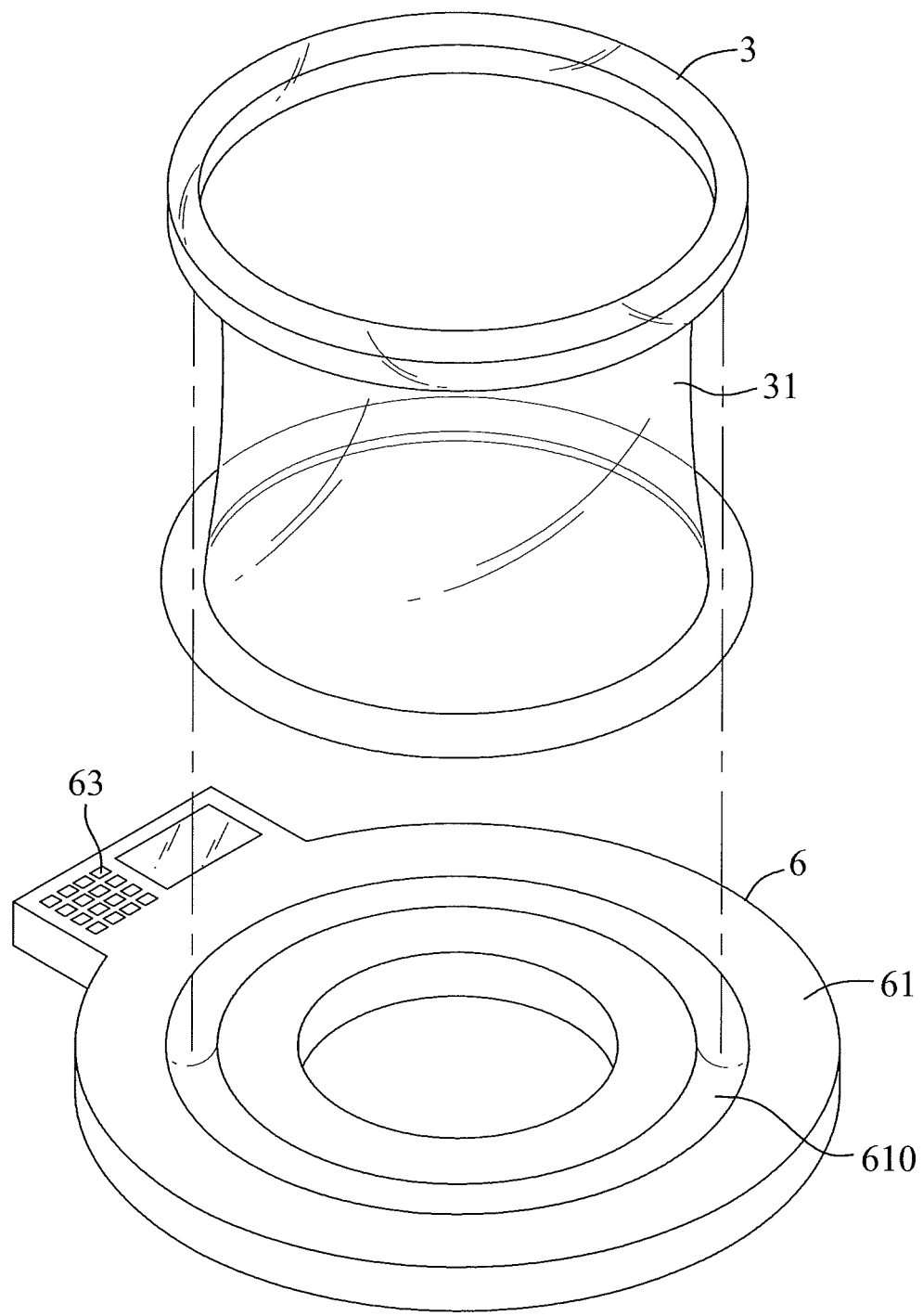
FIG. 1 is a perspective view illustrating a first embodiment of an illuminated surgical retractor system according to the present invention.

Before the present invention is described in greater detail with reference to the accompanying preferred embodiments, it should be noted herein that like elements are denoted by the same reference numerals throughout the disclosure.

Figure 2:
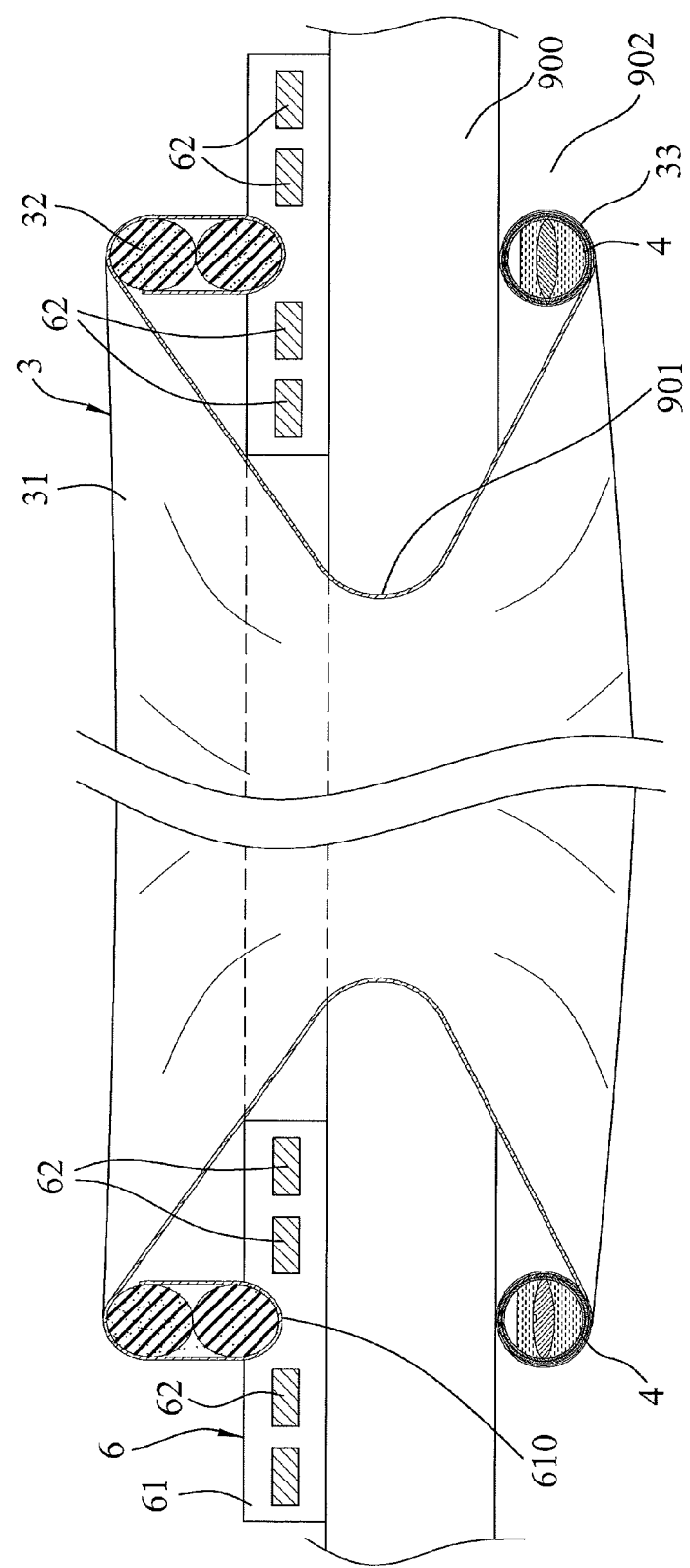
FIG. 2 is a fragmentary partly sectional view of the first embodiment when in use.

Referring to FIG. 1 and FIG. 2, a first embodiment of an illuminated surgical retractor system according to the present invention is configured to retract a surgical incision 901 of a patient 900 for facilitating a surgical operation and to provide illumination into a body cavity 902. The illuminated surgical retractor system comprises a surgical retractor 3, a plurality of illumination devices 4 each of which is disposed in the surgical retractor 3, a power supply unit 5 (see FIG. 3) which is disposed in the surgical retractor 3 and which is coupled electrically to the illumination devices 4 for providing electric power thereto, and a direction control unit 6.

Figure 3:
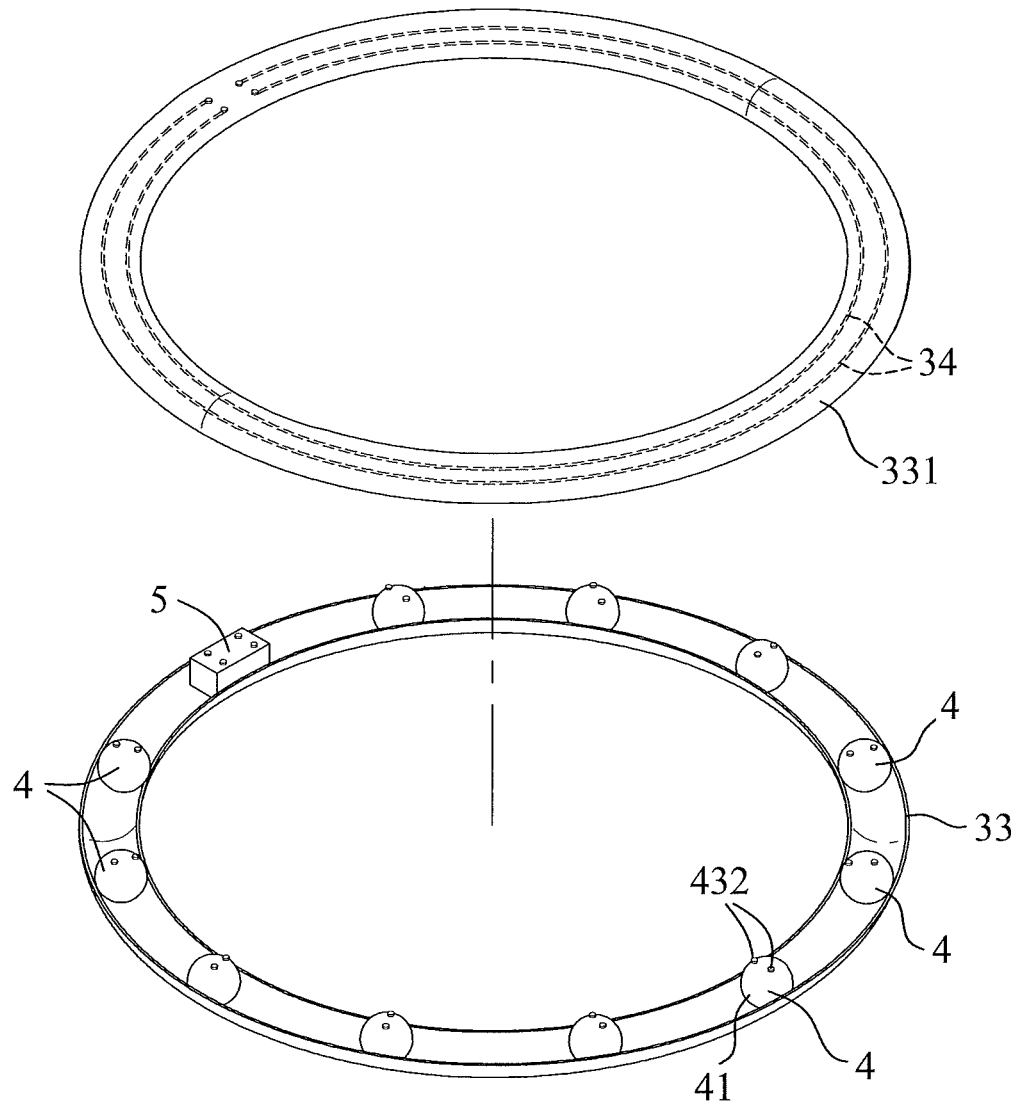
FIG. 3 is an exploded perspective view of an inner ring of the first embodiment.
Figure 4:
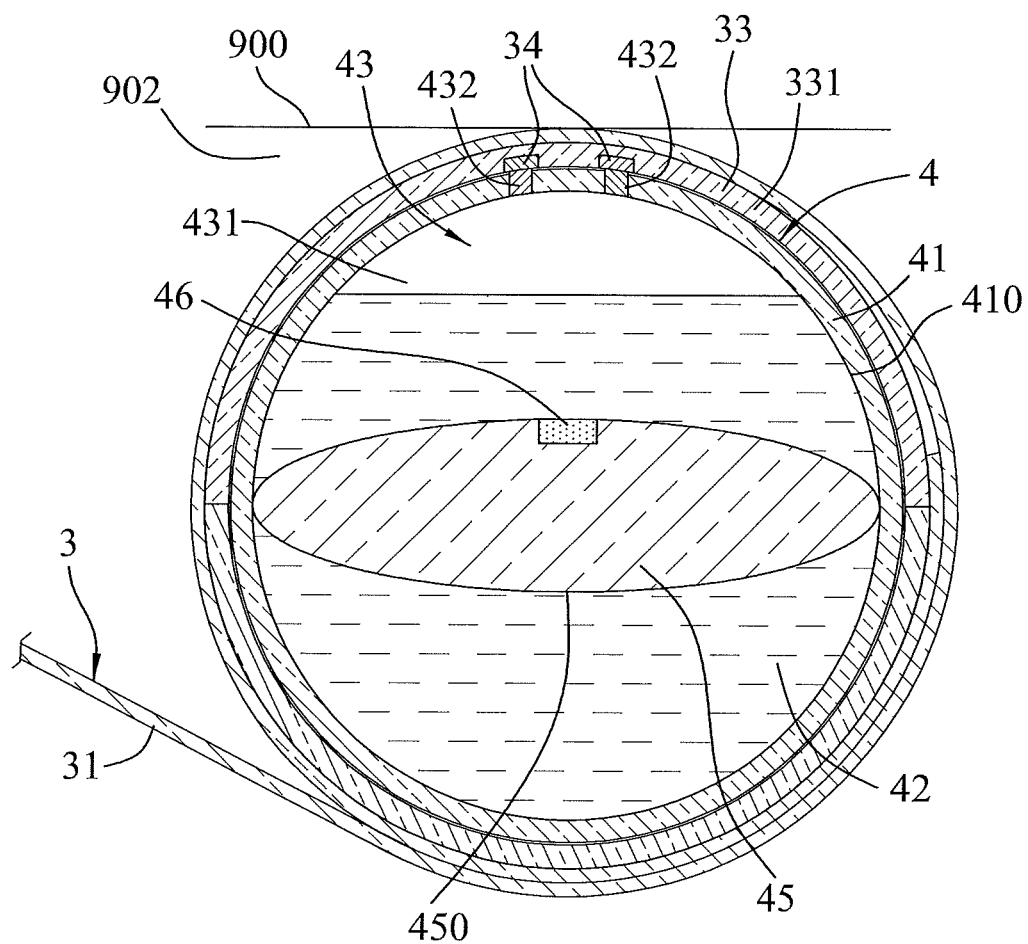
FIG. 4 is a sectional view of an illumination device of the first embodiment which includes a lens element.

Referring to FIGS. 2, 3 and 4, the surgical retractor 3 includes an outer ring 32, a light-transmissive hollow inner ring 33, and a tubular retraction membrane 31 which extends between the output ring 32 and the inner ring 33 and which has a first open end connected to and spread open by the outer ring 32 and a second open end connected to and spread open by the inner ring 33. The tubular retraction membrane 31 is flexible and light-transmissive, and the outer ring 32 and the inner ring 33 are both flexible. The surgical retractor 3 further includes a pair of electrically conductive wires 34 which are mounted to an interior surface of an upper portion 331 of the inner ring 33, and which are spaced apart from each other, and which are coupled electrically to the power supply unit 5. In this embodiment, the outer ring 32 is composed of two rings, and can be rolled into the first open end of the tubular retraction membrane 31 to fold and stretch the tubular retraction membrane 31. However, in practice, there are different ways to fold and stretch the tubular retraction membrane 31 using the outer ring 32, and a structural design of the outer ring 32 is thus not limited to the disclosure herein.

In this embodiment, the illumination devices 4 are disposed in the inner ring 33 at angularly spaced apart positions, and are operable to emit light beams. Each of the illumination devices 4 includes a light-transmissive inner casing 41 which defines a spherical receiving space 410, a light-emitting unit 43 which is disposed in the receiving space 410, which is mounted to a top side of the inner casing 41 and which is coupled electrically to the electrically conductive wires 34, a lens element 45 which is movably disposed in the receiving space 410 and which is rotatable with respect to the inner casing 41, and a magnetic component 46 which is mounted to and disposed at an axis of the lens element 45. The receiving space 410 defined by the inner casing 41 is filled with a liquid 42, and the lens element 45 is suspended in the liquid 42. The magnetic component 46 is responsive to an applied magnetic field to cause the illumination device 4 to change a direction in which the light beam is emitted.

The inner casing 41 is disposed in the inner ring 33. The light-emitting unit 43 includes an electrical contact unit 432 which extends from a lighting member 431 through the inner casing 41 to contact the electrically conductive wires 34. The electrical contact unit 432 makes electrical connection between the light-emitting unit 43 and the power supply unit 5 for transmitting the electric power provided by the power supply unit 5 to the light-emitting unit 43, which is thus driven to emit the light beam toward the lens element 45 disposed in the receiving space 410. The lens element 45 is configured to guide the light beam emitted by the light-emitting unit 43 outwardly of the inner casing 41. In this embodiment, the light-emitting unit 43 is a light-emitting diode (LED), but is not limited to the same in practical implementation.

The disc-shaped lens element 45 is positioned across the path where the light-emitting unit 43 emits the light beam, and has a light exit surface 450 opposite to a surface facing the light-emitting unit 43. The lens element 45 has a diameter substantially equal to an inside diameter of the inner casing 41, and is rotatable with respect to the inner casing 41 to guide the light beam emitted by the light-emitting unit 43 outwardly of the inner casing 41. The magnetic component 46 is one of a magnet and other materials which are attracted to magnets. The magnetic component 46 is driven by the applied magnetic field to rotate the lens element 45 with respect to the light-emitting unit 43, such that the direction in which the light beam propagates outwardly of the inner casing 41 is changed by the lens element 45.

In this embodiment, the lens element 45 is a converging lens, more preferably a biconvex lens as best shown in FIG. 4. However, in practice, the lens element 45 may be one of a plano-convex lens, a positive meniscus lens, Fresnel lens and a liquid lens. Moreover, according to different needs, the lens element 45 may be a diverging lens, such as a biconcave lens, plano-concave lens, a negative meniscus lens, etc. Furthermore, a surface of the lens element 45 may be formed with microstructures that guide light beams, such as prism microlens arrays, hemisphere microlens arrays, pyramid microlens arrays, etc. It should be noted that implementation of the lens element 45 is not limited to the aforementioned disclosure.

Furthermore, even though the magnetic component 46 is disposed at an axis of the lens element 45 in this embodiment, in practice, the magnetic component 46 may be mounted to the lens element 45 in an eccentric manner, such as at a peripheral area of the lens element 45, as long as the magnetic component 46 may be driven by the applied magnetic field to rotate the lens element 45.

Figure 5:
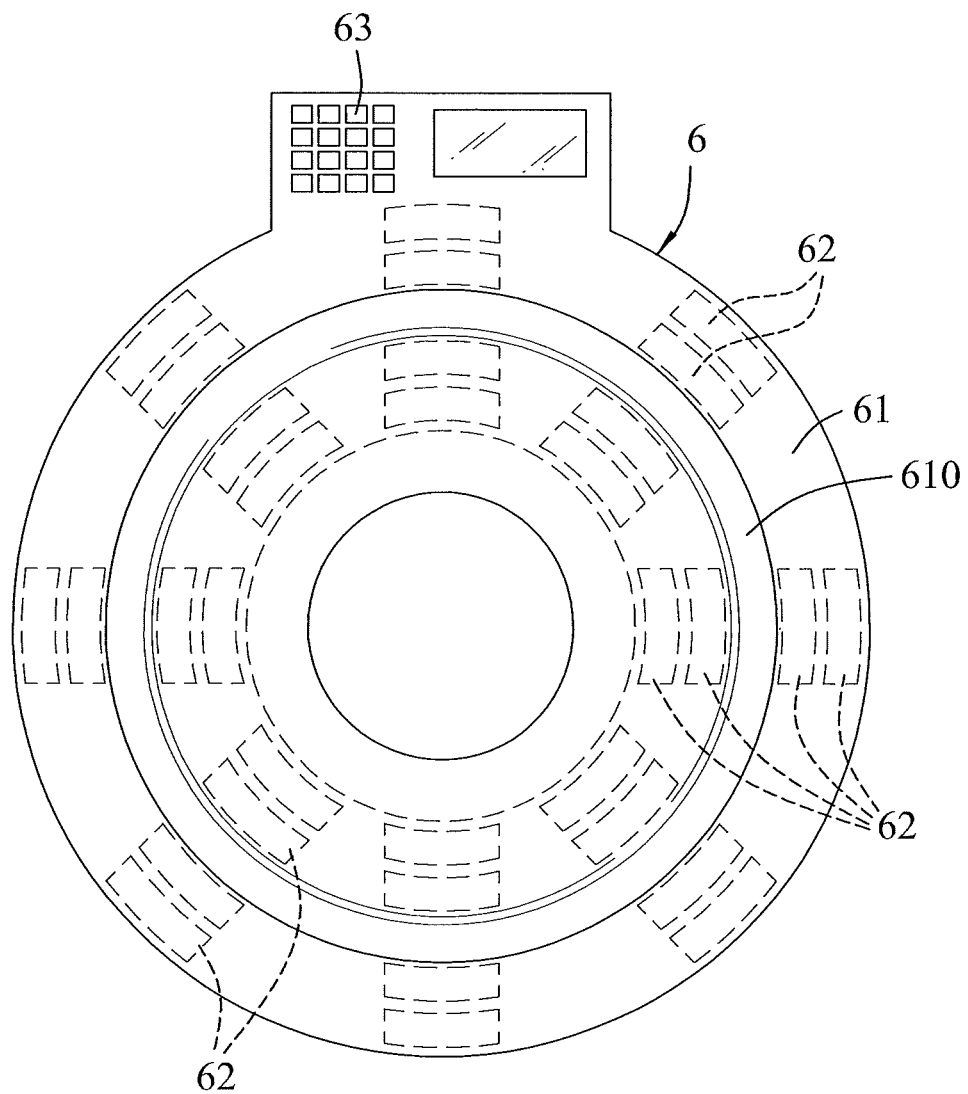
FIG. 5 is a top view of a direction control unit of the first embodiment.

Referring to FIGS. 1, 2 and 5, the direction control unit 6 generates the applied magnetic field. The direction control unit 6 includes a circular ring base 61, a plurality of block-shaped magnet members 62 (e.g., electromagnets) which are spacedly disposed on the base 61, and a controller 63 which is coupled electrically to the magnet members 62 and which is operable to selectively energize the magnet members 62. The base 61 has an inner diameter smaller than those of the outer ring 32 and the inner ring 33, and has a surface that is formed with an annular positioning groove 610 for removable engagement with the outer ring 32.

The magnet members 62 are disposed on the base 61 at angularly spaced apart positions and at radially spaced apart positions, and are disposed respectively inside and outside a projection of the inner ring 33 onto the base 61 (see FIG. 2). In this embodiment, the magnet members 62 are electromagnets 62 which are energized independently of each other to generate the applied magnetic field for driving the magnetic component 46. The controller 63 is operable to adjust the applied magnetic field generated by the electromagnets 62.

Figure 6:
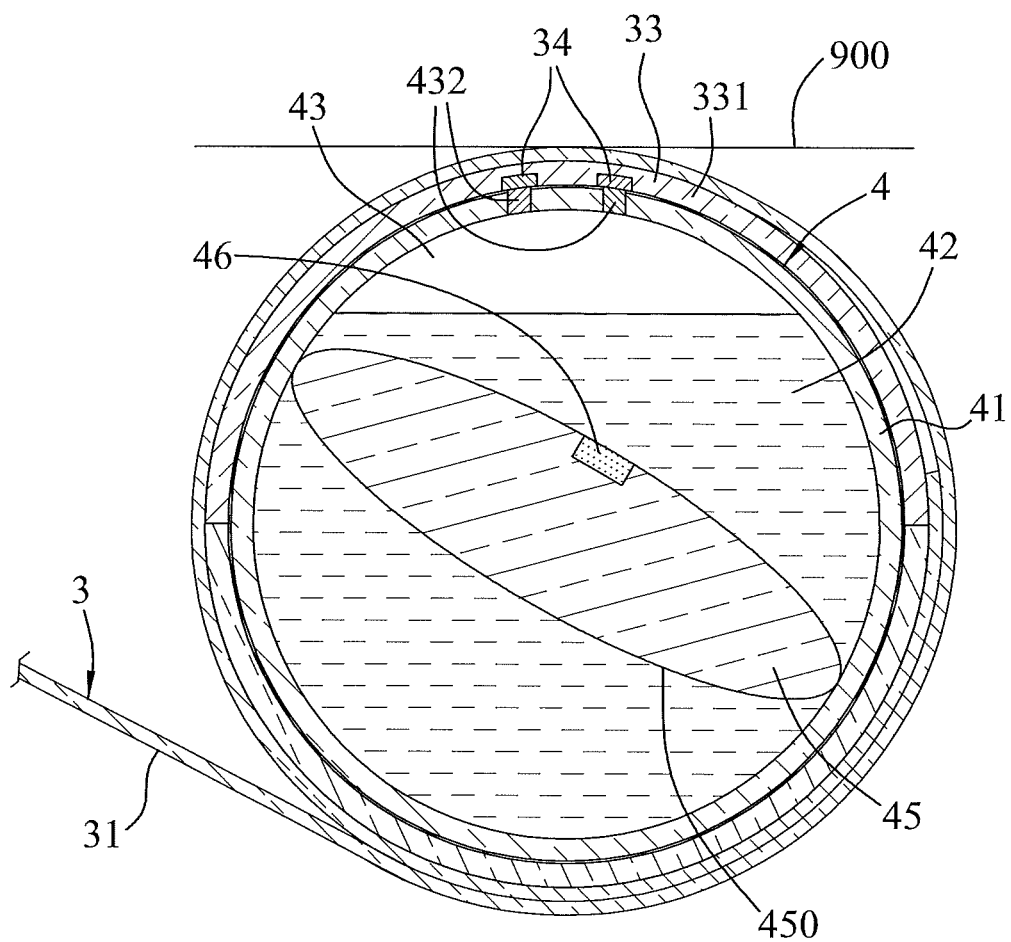
FIG. 6 is a sectional view of the illumination device of the first embodiment, in which the lens element is rotated by an angle.

Referring to FIGS. 2, 5 and 6, during use of the illuminated surgical retractor system of the present invention, the direction control unit 61 is disposed on the patient 900 to encircle the incision 901. Subsequently, the inner ring 33 of the surgical retractor 3 and the second open end of the tubular retraction membrane 31 are disposed through the base 61 and into the body cavity 902, and the outer ring 32 is then rolled into the tubular retraction membrane 31 to fold and stretch the same, such that the tubular retraction membrane 31 is capable of retracting the incision 901 for facilitating the surgical operation.

Based on a position at which a target to be subjected to the surgical operation is located with respect to the inner ring 33, the controller 63 is operable to select a portion of the electromagnets 62 to be energized to generate the applied magnetic field for driving the magnetic component 46 of each of the illumination devices 4 to rotate the lens element 45 with respect to the light-emitting unit 43, such that the direction in which the light beam propagates outwardly of the inner casing 41 is changed by the lens element 45. In this way, the light beams emitted by the illumination devices 4 may be directed to the target to be subjected to the surgical operation, so as to promote brightness of the position where the target is located in the body cavity 902.

For example, for each of the illumination devices 4, the electromagnets 62, which are disposed outside the projection of the inner ring 33 onto the base 61, are energized to generate the applied magnetic field to attract the magnetic component 46 to move toward said electromagnets 62 and to rotate the lens element 45 with respect to the light-emitting unit 43, such that the light exit surface 450 of the lens element 45 is rotated to face a target position that is located inside and beneath the inner ring 33 and away from the direction control unit 6. In this way, the light beams emitted by the illumination devices 4 are focused at the target position so as to promote brightness of a region of the target position.

Alternatively, when the light beams are desired to be directed to a right-hand side of the surgical retractor 3 (see FIG. 2), the electromagnets 62, which are disposed at a right-hand side of the base 61 and inside the projection of the inner ring 33 onto the base 61, are energized to generate the applied magnetic field for rotating the light exit surface 450 of the lens element 45 of each of the illumination devices 4 which are located at a right-hand side of the inner ring 33 to face a target position that is located outside and beneath the right-hand side of the inner ring 33. Similarly, the electromagnets 62, which are disposed at a left-hand side of the base 61 and outside the projection of the inner ring 33 onto the base 61, are energized to generate the applied magnetic field for rotating the light exit surface 450 of the lens element 45 of each of the illumination devices 4 which are located at a left-hand side of the inner ring 33 to face a target position that is located inside and beneath the left-hand side of the inner ring 33. In this way, most of the light beams generated by the light-emitting unit 43 of the illumination devices 4 may be directed to the right-hand side of the surgical retractor 3.

By means of the structural design of the magnetically-controlled illumination devices 4 disposed in the inner ring 33, and the direction control unit 6 which is capable of selectively energizing the electromagnets 62, the direction at which the light beams are emitted by the illumination devices 4 may be adjusted according to different needs during the surgical operation.

In this embodiment, by virtue of the design that the inner casing 41 is filled with the liquid 42, heat generated by the light-emitting unit 43 can be dissipated more effectively, and an effect of smooth rotation of the lens element 45 may be achieved. However, in another embodiment, the inner casing 41 is not necessarily filled with the liquid 42.

Figure 7:
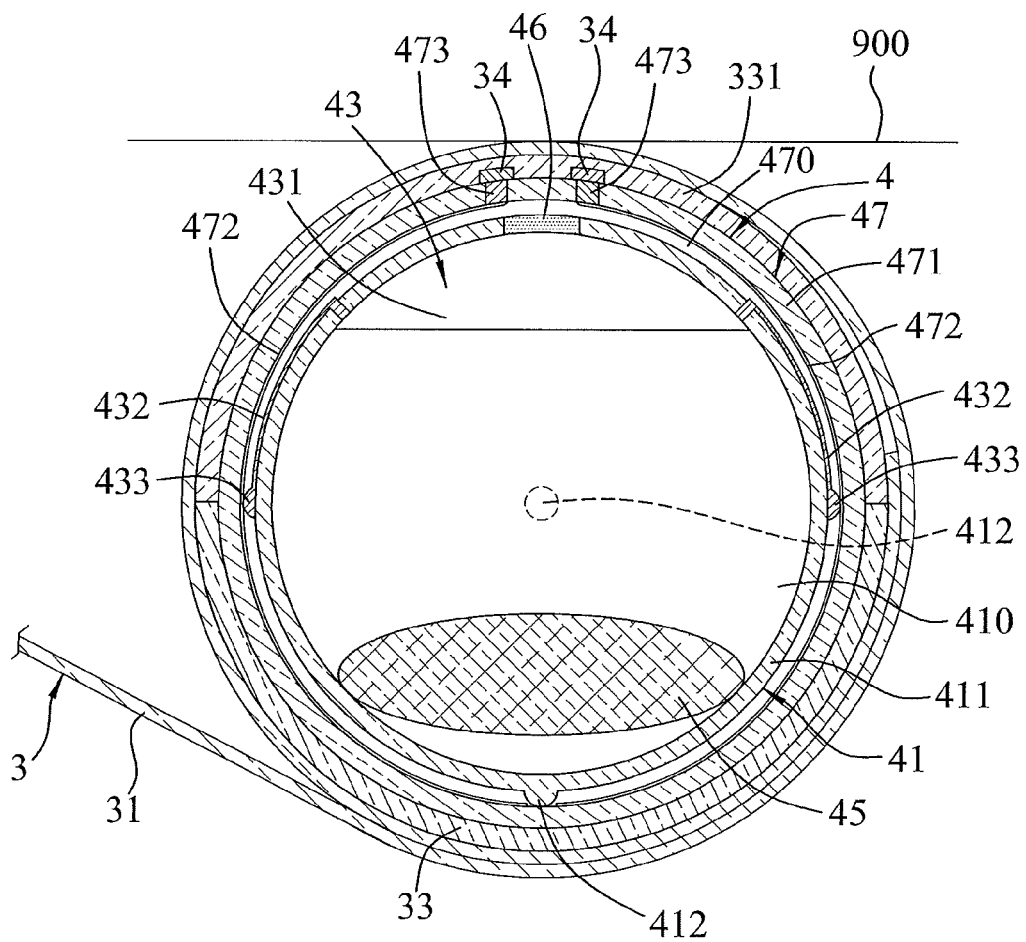
FIG. 7 is a sectional view of an illumination device of a second embodiment of the illuminated surgical retractor system according to the present invention.
Figure 8:
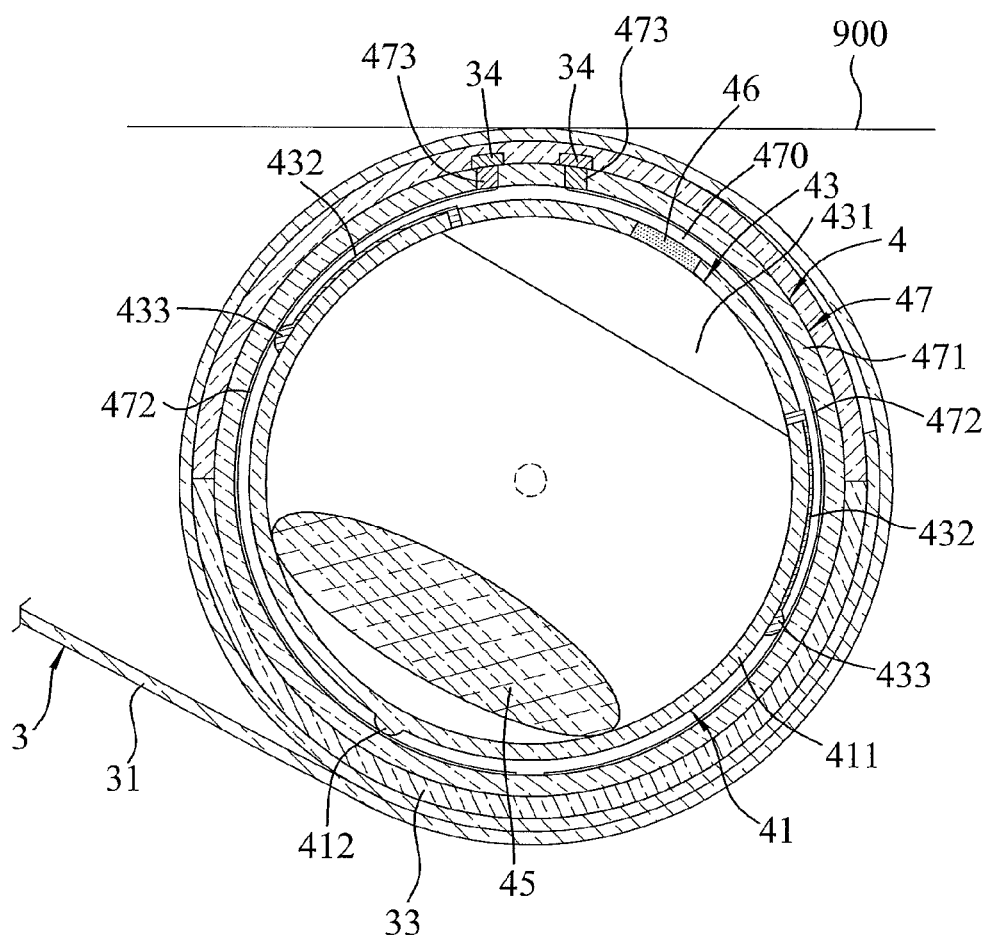
FIG. 8 is a sectional view of the illumination device of the second embodiment, in which an inner casing is rotated by an angle.

Referring to FIG. 7 and FIG. 8, a second embodiment of the illuminated surgical retractor system of the present invention merely differs from the first embodiment in the structural design of the illumination device 4. For the sake of brevity, only differences between the second embodiment and the first embodiment are illustrated hereinafter.

In this embodiment, each of the illumination devices 4 includes an outer casing unit 47, a light-transmissive inner casing 41, a light-emitting unit 43, a lens element 45 and a magnetic component 46. The outer casing unit 47 is disposed in the inner ring 33, and is coupled electrically to the electrically conductive wires 34. The outer casing unit 47 includes a light-transmissive outer casing 471 that defines a spherical space 470. The light-transmissive inner casing 41 is movably disposed in the spherical space 470 and is rotatable with respect to the outer casing unit 47. The inner casing 41 defines a receiving space 410. The light-emitting unit 43 is mounted in the inner casing 41 at a first side of the receiving space 410, and is configured to emit the light beam toward a second side opposite to the first side of the receiving space 410. The lens element 45 is mounted to the inner casing 41 at a position corresponding to the light-emitting unit 43, i.e. the second side of the receiving space 410. The lens element 45 is configured to guide the light beam emitted by the light-emitting unit 43 outwardly of the inner casing 41 and the outer casing 471. The magnetic component 46 is mounted to the inner casing 41 adjacent to the direction control unit 6.

The outer casing unit 47 further includes a transparent electrically conductive unit provided on an interior surface of the outer casing 471, and a conductive contact unit 473 coupled electrically to the transparent electrically conductive unit and extending through the outer casing 471 so to couple electrically with the power supply unit 5. Specifically, the transparent electrically conductive unit includes a pair of transparent conducting films 472 that have substantially semispherical shapes and that are substantially symmetrical with each other. The conductive contact unit 473 is coupled electrically to the electrically conductive wires 34 so as to transmit the electric power provided by the power supply unit 5 to the transparent conducting films 472.

The inner casing 41 includes a light-transmissive spherical body 411 that has a spherical shape corresponding to the spherical space 470 defined by the outer casing 471, that is rotatable with respect to the outer casing 471, and that is disposed inside the spherical space 470 in a manner that the inner casing 41 is concentric with the spherical space 470. The inner casing 41 further includes a plurality of support members 412 which are formed on the spherical body 411 at diametrically opposite positions of the spherical body 411. The support members 412 project outwardly and away from the spherical body 411 and movably abut against the transparent conducting films 472, respectively. The disposition of the support members 412 ensures that the inner casing 41 is concentric with the spherical space 470.

The light-emitting unit 43 includes a lighting member 431 which is disposed at a top side in the receiving space 410, and which emits the light beam downwardly toward the lens element 45 (see FIG. 7). The light-emitting unit 43 further includes an electrical contact unit 432 which extends from the lighting member 431 through the inner casing 41 and to an exterior surface of the inner casing 41. The electrical contact unit 432 makes electrical connection between the lighting member 431 and the transparent electrically conductive unit (i.e., the transparent conducting films 472). The electrical contact unit 432 includes a pair of electrical contacts 433 located respectively at diametrically opposite positions of the exterior surface of the spherical body 411 of the inner casing 41. The electrical contacts 433 project away from the spherical body 411 of the inner casing 41, and movably abut against a respective one of the transparent conducting films 472, so as to transmit the electric power for driving the lighting member 431. Moreover, by virtue of the projecting design of the electrical contacts 433, the support members 412 may cooperate with the electrical contacts 433 to ensure that the spherical body 411 is concentric with the spherical space 470 while the inner casing 41 is rotating in the spherical space 470.

The lens element 45 is non-rotatably mounted in the receiving space 410 for guiding the light beam emitted by the lighting member 431 outwardly (e.g., downwardly) of the inner casing 41 and the outer casing unit 47. The magnetic component 46 is mounted to a top side of the spherical body 411.

Referring to FIG. 5, when the direction in which the light beams are emitted by the illumination devices 4 is desired to be changed, the controller 63 is operable to selectively energize the magnet members 62 to generate the applied magnetic field. When the magnetic component 46 of the illumination device 4 is driven by the applied magnetic field to rotate the inner casing 41 with respect to the outer casing unit 47, the light-emitting unit 43 moves together with the lens element 45 such that the direction in which the light beam is emitted outwardly of the outer casing 471 is changed.

Since the transparent conducting films 472 have substantially semispherical shapes and are substantially symmetrical with each other, since the electrical contacts 433 are located respectively at diametrically opposite positions of the exterior surface of the spherical body 411 of the inner casing 41, and since the spherical body 411 is concentric with the spherical space 470, the electrical connection between each of the electrical contacts 433 and a respective one of the transparent conducting films 472 may be maintained when the inner casing 41 is rotating with respect to the outer casing 471, such that the lighting member 431 is able to continuously emit the light beam.

In this embodiment, the pair of electrical contacts 433 and three support members 412 are used to ensure that the spherical body 411 is concentric with the spherical space 470. However, in practice, the number of the support members 412 is not limited to the disclosure herein, and only one support member 412 may be formed on a bottom side of the spherical body 411, such that the support member 412 cooperates with the pair of electrical contacts 433 to form a three-point support for ensuring that the spherical body 411 is concentric with the spherical space 470 within a confined range of rotation angle.

Further, it should be noted that, in the first and second embodiments, the magnet members 62 of the direction control unit 6 which are disposed inside and outside of the projection of the inner ring 33 onto the base 61 are utilized to control the direction in which the light beams are emitted. However, in practice, the direction control unit 6 may not necessarily include the base 61. That is to say, the disposition of the magnet members 62 is not limited to the base 61, and may be arranged freely based on the needs of the surgical operation, for example, the magnet members 62 may be directly disposed on the body of the patient 900 as long as the magnetic component 46 may be driven by the applied magnetic field generated by the magnet members 62 for changing the direction in which the light beams are emitted. Moreover, the magnet members 62 may be permanent magnets, and may also change the direction in which the light beams are emitted without being energized.

Moreover, in a configuration of the present invention, the magnet members 62 have annular shapes, and are disposed on the base 61 at concentrically spaced apart positions. Preferably, the magnet members 62 have varying sizes, and an innermost one of the magnet members 62 is surrounded by other ones of the magnet members 62. The annular magnet members 62 are disposed inside and outside the projection of the inner ring 33 onto the base 61, and are operable to control rotation of the lens element 45 or the inner casing 41, such that the light beams emitted by the illumination devices 4 may be directed to a target position that is located inside and beneath the inner ring 33 or to separate positions that are located outside and beneath the inner ring 33.

In another configuration, the annular magnet members 62 are disposed on the base 61 in a non-concentric manner such that one of the magnet members 62 may have a first part that is located inside the projection of the inner ring 33 onto the base 61, and a second part that is located outside the projection of the inner ring 33 onto the base 61. By this design, most of the illumination devices 4 may emit light beams toward the same direction. Said one of the magnet members 62 may cooperate with other ones of the magnet members 62 that are also arranged in a non-concentric manner to achieve more complex control of directions in which the light beams are emitted.

Figure 9:
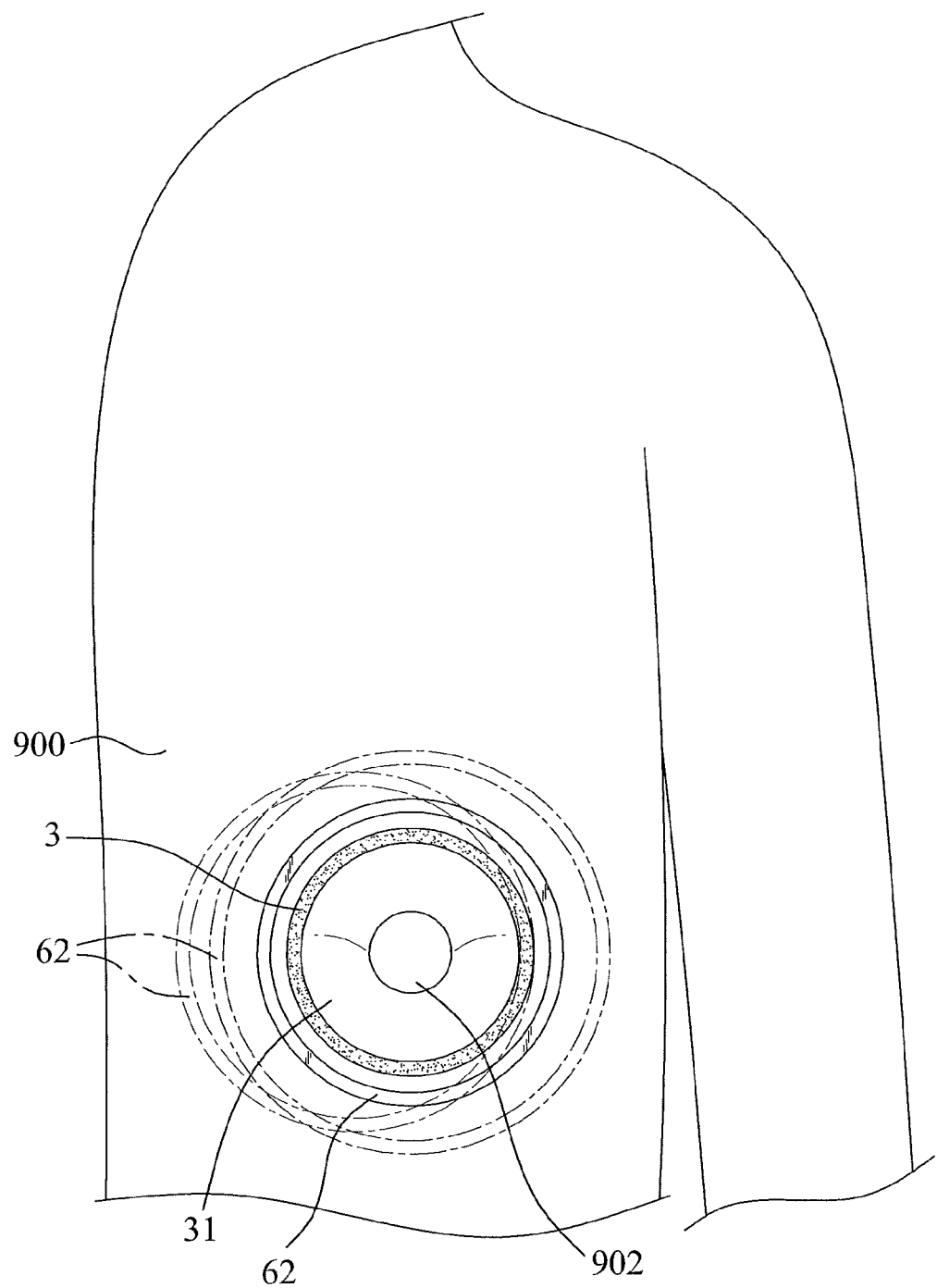
FIG. 9 is a top view of the illuminated surgical retractor system, in which a ring-shaped magnetic member is directly disposed on a patient's body when in use.
Figure 10:
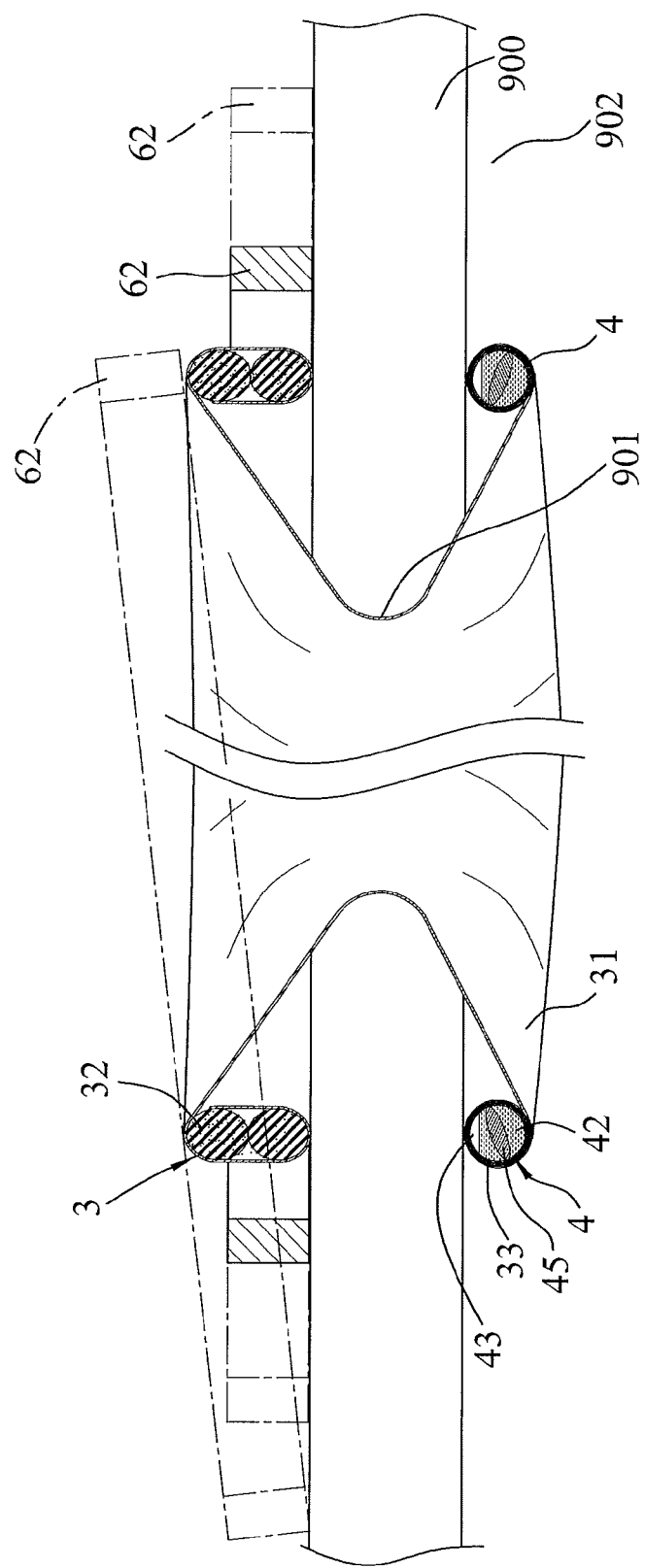
FIG. 10 is a fragmentary partly sectional view of the illuminated surgical retractor system illustrating a position of the ring-shaped magnetic member with respect to the illumination device.

Referring to FIG. 9 and FIG. 10, in practice, in a condition that the base 61 is omitted, the annular magnet members 62 are disposed adjacent to and above the surgical retractor 3, and generate the applied magnetic field to control the direction in which the light beams are emitted by the illumination devices 4. In use, the magnet members 62 may be displaced arbitrarily with respect to the illumination devices 4 so as to change the direction in which the light beams are emitted according to different needs.

Figure 11:
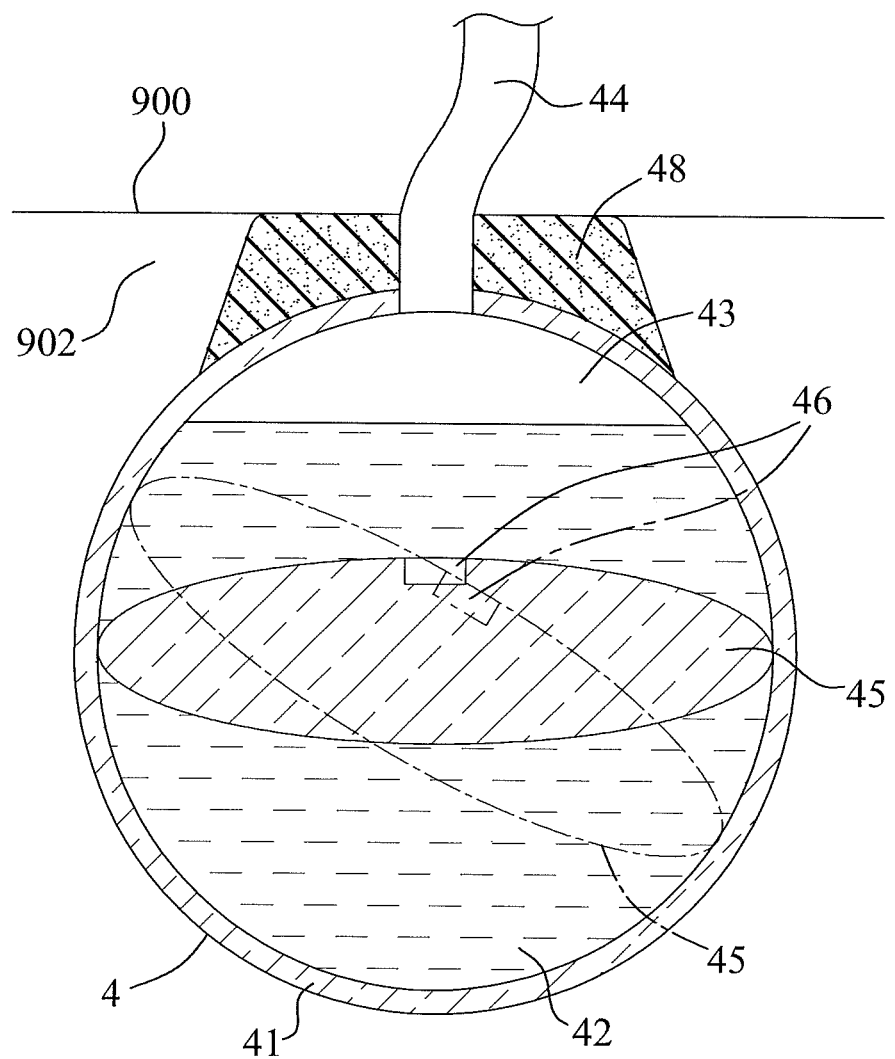
FIG. 11 is a sectional view of the illumination device of the first embodiment which is used separately from a surgical retractor.
Figure 12:
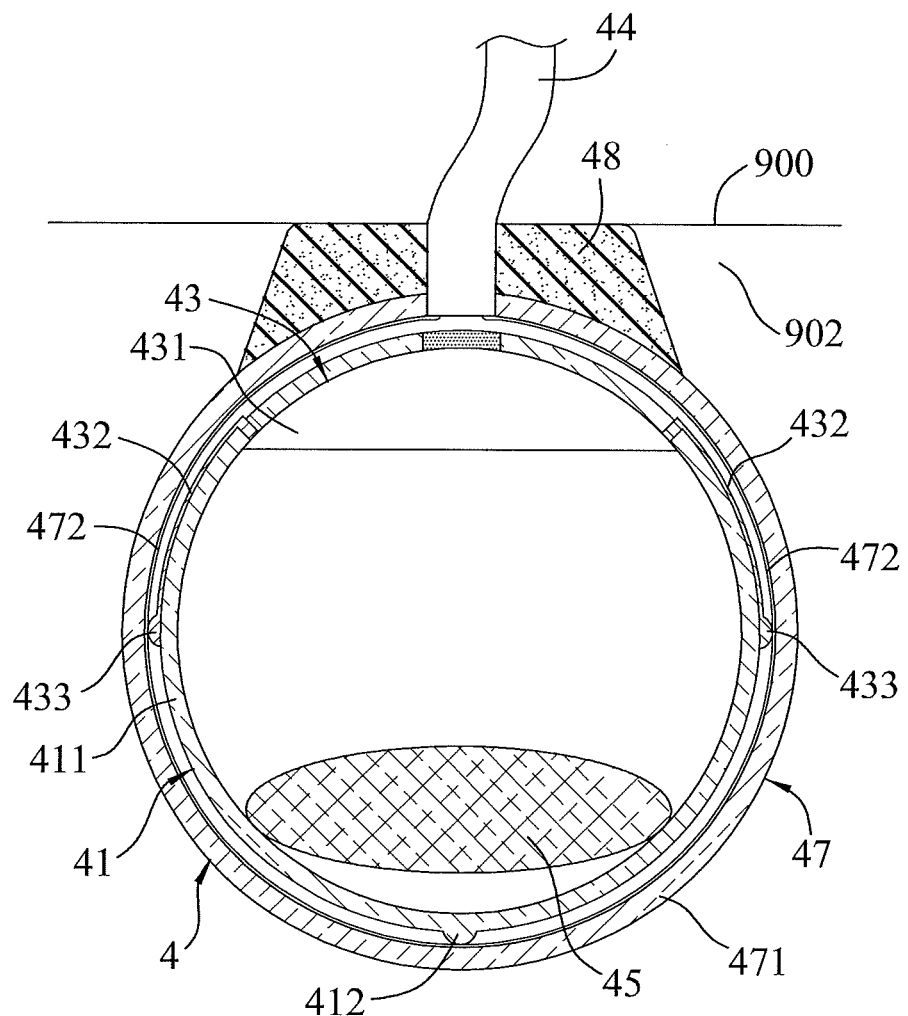
FIG. 12 is a sectional view of the illumination device of the second embodiment which is used separately from the surgical retractor.

Referring to FIG. 11 and FIG. 12, in the present invention, the illumination devices 4 may be used individually, and are not necessarily disposed in the surgical retractor 3. A first embodiment and a second embodiment of a magnetically-controlled illumination device 4 that can be used individually are illustrated in the following paragraphs.

Referring to FIG. 11, the first embodiment of the magnetically-controlled illumination device 4 further includes a pull cord 44 which has one end attached to the inner casing 41, and a fixing member 48, such as a rubber pad, which is mounted on a top side of the exterior surface of the inner casing 41. Specifically, the pull cord 44 is a power cord which extends through the inner casing 41, which is coupled electrically to the light-emitting unit 43, and which is configured to transmit electric power thereto. The fixing member 48 is used to secure said end of the pull cord 44 to the inner casing 41. During the surgical operation, after the magnetically-controlled illumination device 4 has been disposed in the body cavity 902, the pull cord 44 may be pulled outwardly of and through the body cavity 902 by using a puncture needle (not shown). The pull cord 44 is coupled electrically to an external power supply (not shown). By means of pulling the pull cord 44, the fixing member 48 may abut against an interior surface of the body cavity 902. Therefore, the pull cord 44 is provided for a pulling purpose and a power transmission purpose. In practice, the fixing member 48 may be omitted.

Based on different needs of a surgical operation, the body cavity 902 may be disposed with a plurality of the magnetically-controlled illumination devices 4. Subsequently, according to a desired direction in which the beams are emitted, by placing the magnet members 62 directly or the direction control unit 6 upon the body of the patient 900, the applied magnetic field generated by the magnet members 62 may drive the magnetic component 46 to rotate the lens element 45 in the illumination devices 4, so as to direct the light beams emitted thereby toward the desired direction.

Similarly, referring to FIG. 12, the second embodiment of the magnetically-controlled illumination device 4 that is used individually further includes a pull cord 44 which has one end attached to the outer casing 471, and a fixing member 48 which is mounted on a top side of an exterior surface of the outer casing 471 and which is used to cover and secure said end of the pull cord 44 to the outer casing 471. Specifically, the pull cord 44 is a power cord which extends through the outer casing 471, and which is coupled electrically to the transparent conducting films 472 for transmitting electric power to the lighting member 431 via the electrical contact unit 432. Similarly, the pull cord 44 may be pulled outwardly of and through the body cavity 902, and is coupled electrically to an external power supply. By means of pulling the pull cord 44, the fixing member 48 may abut against the interior surface of the body cavity 902. By placing the magnet members 62 directly or the direction control unit 6 upon the body of the patient 900, the applied magnetic field may adjust the direction in which the light beams are emitted.

In practical implementation, the pull cord 44 used in the first embodiment and the second embodiment of the magnetically-controlled illumination device 4 is not necessarily provided with the function of transmitting electric power, and may be a simple rope for the pulling purpose. The rope may be directly secured to the inner casing 41 (the first embodiment) or the outer casing 471 (the first embodiment). The light-emitting unit 43 may be modified to be powered by a built-in battery (not shown). When the built-in battery is utilized in the light-emitting unit 43 of the second embodiment of the magnetically-controlled illumination device 4, the transparent conducting films 472 of the outer casing unit 47 may be omitted, and the electrical contact unit 432 of the light-emitting unit 43 may be also omitted. Moreover, the spherical body 411 of the inner casing 41 is not necessarily formed with the support members 412. In other words, the inner casing 41 is not necessarily concentric with the spherical space 470.

To sum up, by virtue of the magnetic component 62 provided in each of the illumination devices 4 which are disposed in the inner ring 33 of the surgical retractor 3, the direction in which the light beams are emitted may be adjusted according to the applied magnetic field, so as to satisfy different needs for illumination. In this way, the light beams emitted by the illumination devices 4 may be directed to the desired direction, thereby providing sufficient illumination on a specific portion in the body cavity 902. Furthermore, by virtue of the direction control unit 6 which may be operable to selectively energize the magnet members 62 (i.e., the electromagnets), the direction in which the light beams are emitted may be adjusted with ease, so as to promote the quality of surgical operations.

While the present invention has been described in connection with what are considered the most practical embodiments, it is understood that this invention is not limited to the disclosed embodiments but is intended to cover various arrangements included within the spirit and scope of the broadest interpretation so as to encompass all such modifications and equivalent arrangements.

The invention claimed is:

1. An illuminated surgical retractor system comprising:
   a surgical retractor including an outer ring, a light-transmissive hollow inner ring, and a tubular retraction membrane which extends between said outer ring and said inner ring and which has a first open end connected to and spread open by said outer ring and a second open end connected to and spread open by said inner ring; and
   at least one illumination device disposed in said inner ring and operable to emit a light beam, said illumination device including a magnetic component which is responsive to an applied magnetic field to cause said illumination device to change a direction in which the light beam is emitted.

2. The illuminated surgical retractor system according to claim 1, wherein said illumination device further includes:
   a light-transmissive inner casing defining a receiving space;
   a light-emitting unit mounted to said inner casing and configured to emit the light beam toward the receiving space; and
   a lens element movably disposed in the receiving space and rotatable with respect to said inner casing, said lens element being configured to guide the light beam emitted by said light-emitting unit outwardly of said inner casing;
   wherein said magnetic component is mounted to said lens element and is driven by the applied magnetic field to rotate said lens element with respect to said light-emitting unit, such that the direction in which the light beam propagates outwardly of said inner casing is changed by said lens element.

3. The illuminated surgical retractor system according to claim 2, further comprising a power supply unit which is disposed in said inner ring and which is coupled electrically to said light-emitting unit of said illumination device for providing electric power thereto.

4. The illuminated surgical retractor system according to claim 2, wherein the receiving space defined by said inner casing is filled with a liquid, and said lens element is suspended in the liquid.

5. The illuminated surgical retractor system according to claim 2, wherein said lens element is one of a diverging lens and a converging lens.

6. The illuminated surgical retractor system according to claim 1, wherein said illumination device further includes:
   an outer casing unit including a light-transmissive outer casing which defines a spherical space;
   a light-transmissive inner casing movably disposed in the spherical space and rotatable with respect to said outer casing unit, said inner casing defining a receiving space;
   a light-emitting unit mounted to said inner casing, and configured to emit the light beam toward the receiving space; and
   a lens element mounted to said inner casing at a position corresponding to said light-emitting unit, said lens element being configured to guide the light beam emitted by said light-emitting unit outwardly of said inner casing and said outer casing;
   wherein said magnetic component is mounted to said inner casing and is driven by the applied magnetic field to rotate said inner casing with respect to said outer casing unit and thereby move said light-emitting unit together with said lens element such that the direction in which the light beam is emitted outwardly of said outer casing is changed.

7. The illuminate surgical retractor system according to claim 6, further comprising a power supply unit which is disposed in said inner ring and which is coupled electrically to said illumination device;
  wherein said outer casing unit of said illumination device further includes a transparent electrically conductive unit provided on an interior surface of said outer casing, and a conductive contact unit coupled electrically to said transparent electrically conductive unit and extending through said outer casing so as to couple electrically with said power supply unit; and
wherein said light-emitting unit of said illumination device includes a lighting member which is disposed in the receiving space, and an electrical contact unit which extends from said lighting member through said inner casing and to an exterior surface of said inner casing, said electrical contact unit making electrical connection between said lighting member and said transparent electrically conductive unit.

8. The illuminated surgical retractor system according to claim 7, wherein said inner casing has a spherical shape corresponding to the spherical space, and is disposed inside the spherical space in a manner that said inner casing is concentric with the spherical space, said transparent electrically conductive unit including a pair of transparent conducting films that have substantially semispherical shapes and that are substantially symmetrical with each other, said electrical contact unit including a pair of electrical contacts located respectively at diametrically opposite positions of the exterior surface of said inner casing, said electrical contacts projecting away from said inner casing and movably abutting against a respective one of said transparent conducting films.

9. The illuminated surgical retractor system according to claim 8, wherein said inner casing is formed with at least one support member which projects outwardly and away from said inner casing and which movably abuts against one of said transparent conducting films, said support member cooperating with said electrical contacts to ensure that said inner casing is concentric with the spherical space.

10. The illuminated surgical retractor system according to claim 1, further comprising at least one magnet member which generates the applied magnetic field.

11. The illuminated surgical retractor system according to claim 10, wherein said magnet member is one of a permanent magnet and an electromagnet.

12. The illuminated surgical retractor system according to claim 10, wherein said magnet member has one of a block shape and an annular shape.

13. The illuminated surgical retractor system according to claim 1, further comprising a direction control unit which generates the applied magnetic field, said direction control unit including a base, and a plurality of electromagnets which are spacedly disposed on said base and which are energized independently of each other to generate the applied magnetic field.

14. The illuminated surgical retractor system according to claim 13, wherein said electromagnets are annular in shape and have varying sizes, an innermost one of said electromagnets being surrounded by other ones of said electromagnets.

15. The illuminated surgical retractor system according to claim 13, wherein said base is annular in shape, and said electromagnets are disposed on said base at angularly spaced apart positions.

16. The illuminated surgical retractor system according to claim 13, wherein said direction control unit further includes a controller which is coupled electrically to said electromagnets and which is operable to selectively energize said electromagnets.

17. The illuminated surgical retractor system according to claim 13, wherein said base has a surface that is formed with an annular positioning groove for removable engagement with said outer ring.

18. A magnetically-controlled illumination device comprising:
  a light-transmissive inner casing defining a receiving space;
  a light-emitting unit mounted to said inner casing and configured to emit a light beam toward the receiving space;
  a lens element movably disposed in the receiving space and rotatable with respect to said inner casing, said lens element being configured to guide the light beam emitted by said light-emitting unit outwardly of said inner casing; and
a magnetic component mounted to said lens element, and driven by an applied magnetic field to rotate said lens element with respect to said light-emitting unit such that a direction in which the light beam propagates outwardly of said inner casing is changed by said lens element.

19. The magnetically-controlled illumination device according to claim 18, further comprising a pull cord which has one end attached to said inner casing, and which is a power cord coupled to said light-emitting unit for transmitting electric power thereto.

20. A magnetically-controlled illumination device comprising:
  an outer casing unit including a light-transmissive outer casing which defines a spherical space;
  a light-transmissive inner casing movably disposed in the spherical space and rotatable with respect to said outer casing unit, said inner casing defining a receiving space;
  a light-emitting unit mounted to said inner casing, and configured to emit the light beam toward the receiving space;
  a lens element mounted to said inner casing at a position corresponding to said light-emitting unit, said lens element being configured to guide the light beam emitted by said light-emitting unit outwardly of said inner casing and said outer casing; and
a magnetic component mounted to said inner casing, and driven by an applied magnetic field to rotate said inner casing with respect to said outer casing unit and thereby move said light-emitting unit together with said lens element such that the direction in which the light beam is emitted outwardly of said outer casing is changed.

\* \* \* \* \*